US00PP08950P

United States Patent [19]

Friday

[11] Patent Number: Plant 8,950

[45] Date of Patent: Oct. 18, 1994

[54] P.F. 12A PEACH TREE

[76] Inventor: Paul J. Friday, P.O. Box 850, Coloma, Mich. 49038

[21] Appl. No.: 96,267

[22] Filed: Jul. 26, 1993

[51] Int. Cl.[5] ..... A01H 5/00
[52] U.S. Cl. ..... Plt./43.2
[58] Field of Search ..... Plt. 43.2

[56] References Cited

PUBLICATIONS

Register of New Fruit & Nut Varieties 1972 Brooks et al (ed) U of Calif. Press pp. 430–431.

*Primary Examiner*—Patricia R. Moody
*Attorney, Agent, or Firm*—Fred P. Kostka

[57] ABSTRACT

A new and distinct variety of peach tree having the following unique combination of desirable features:

1. Producing a very form fruit.
2. A unique partially showy blossom.
3. A substantially spheroidal fruit with an attractive red skin covering about 80% of the surface at maturity.
4. A fruit maturing about 4 days later than the Redhaven peach.
5. A fruit of good quality and taste.

1 Drawing Sheet

ORIGIN OF VARIETY

The new variety of peach tree (hereinafter referred to as the P.F. 12A peach tree) was originated by Paul Friday in the experimental orchard maintained for the purpose of breeding peaches at Paul Friday Farms Inc. located in Coloma, Mich. Coloma is located in the southwest section of Michigan. The P.F. 12A peach tree was developed in a first generation cross between two seedlings.

The female parent and the male parent originated from deliberately selected ones of peach trees of unknown origin grown in the peach tree breeding orchard of Paul Friday Farms Inc. for about 8 years. The seedlings were grown in the experimental orchard of the Paul Friday Farms Inc.

ASEXUAL REPRODUCTION OF THE VARIETY

The new and distinct variety of peach tree was asexually propagated by budding as performed in the experimental orchard of Paul Friday Farms Inc. located in Coloma, Mich. The asexual propagaion demonstrates that such reproduction of the characteristics of the tree are consistent and are established and transmitted through succeeding propagation.

SUMMARY OF THE VARIETY

The new and distinst variety of peach tree is of moderate large upright growth and a regular and productive bearer of peaches. The blossoms are characterized by being contracted or partially open when in full bloom so as to be capable of being described as partially nonshowy. At the same time the petals of the blossoms are of lesser length than the length of petals of the normal showy blossom as exemplified by the Loring peach blossom.

The blossoms of the present peach tree are clearly distinguisable from the non-showy blossom of the Redhaven peach tree and showy blossom of the Loring peach tree. The typical non-showy as represented by the Redhaven includes five relatively short petals angularly spaced and radially projecting upwardly from the blossom base. the diametrical distance across the blossoms between the petal edges is about 1 inch.

The typical showy blossom as exemplified by the Loring peach blossom includes five petals of substantial greater length and being angularly spaced and radially projecting normal to the base to form what may best be described as a generally flat blossom or flower. The diameter of the Loring blossom or flower taken between the outer edges of the petals is about 1-7/16 inches.

In contrast, the blossoms of the present tree include five petls each of which are somewhat but distinctively curled about their lengthwise axis in the form of an elongate concave cup. The cup-shaped petals are angularly spaced and project upwardly from the blossom base. The diameter of the blossom taken between the edges of oppositely disposed petals is of a length about midway the length of the Loring and the Redhaven peach blossom.

The fruit has a firm flesh and may be described as resilient to the extent that the flesh is yieldable and restorable to its original state when subjected to impact forces which may cause permanent deformation in peaches of the commercial varieties. The firmness of the fruit facilitates handling and packaging of the peaches without damaging the same for shipment. This results in less spoilage and also increases the shelf life.

The fruit matures in the early part of the peach growing season of Southwestern Michigan. The fruit as mentioned heretofore is of red color over about 80% of its spheroidal surface and has a very attractive appearance.

BRIEF DESCRIPTION OF THE PHOTOGRAPHS

The accompanying photographic illustrations show a typical specimen of the fruit and the foliage of the new variety, with the upper and lower surface of the leaves and an exterior and sectional view of the fruit with the stone removed. The illustrations were taken shortly after being picked at maturity (firm ripe) and the colors as nearly true as reasonably possible in a photographic color representation.

DESCRIPTION OF VARIETY

The detailed botanical description of the foliage and fruit of the new variety of peach tree is based upon observations of the specimens grown at Coloma, Mich.

with the color terminology, other than the terminology expressed in common terms, in accordance with the Panatone Matching System (PMS) as used internationally to identify printed colors.

Tree:
- *Height.*—Unpruned 14'.
- *Width.*—Unpruned 12'.
- *Size.*—Medium-large.
- *Vigor.*—Medium vigor, 2' to 3' per year.
- *Density.*—Medium, pruning requirement heavy.
- *form.*—Upright.
- *Production.*—Productive, approximately 1/10 of the fruit annually.
- *Bearer.*—Consistent.
- *Disease resistance to bacterial leaf and fruit spot.*—Good.

Trunk:
- *size.*—Medium.
- *Surface.*—Smooth to medium shaggy.

Branches:
- *Size.*—Medium.
- *Surface.*—Smooth to medium.
- *Lenticels.*—Medium number and medium size.
- *Color.*—Grayish brown.

Leaves:
- *Size.*—Medium. Average length — 5½—. Average width — 1½".
- *Form.*—Lanceolate — pointed.
- *Thickness.*—Medium.
- *Texture.*—Medium.
- *Margin.*—Serrate.
- *Petiole.*—Medium length-medium thickness.

Gland: Number varies from 3–7. Average 4. Located on base of leaf and upper portion of petiole.
- *Color.*—Upper surface: green (350c).
- *Surface.*—Dull green (349c).
- *Flower buds.*—Size: Medium. Length: Medium. Flowers.—Blooming period: Apr. 7, 1992 to Apr. 14, 1992. Size: Medium or partially showy inclined upright petal pattern (about 1" diameter). Pollen: Present, self-fertilizing. Color: Pink.

Fruit:
- *Maturity when described.*—Firm ripe.
- *Date of first picking.*—Aug. 5, 1992 (About 4 days after picking Redhaven — Aug. 1, 1992. Fruit matures very evenly and can be picked in two pickings.)
- *Date of last picking.*—Aug. 9, 1992.
- *Size.*—Large sphere. Average diameter — 2¾.
- *Form:* Spherical.
- *Suture.*—Very shallow.

Skin:
- *Thickness.*—Medium.
- *Texture.*—Tough, tenacious to skin.
- *Tendency to crack.*—None.
- *Down.*—Moderate to little.
- *Color.*—Yellow ground color (134c). Nearly overspread (80%) with red (174c) to (173c).

Flesh:
- *Texture.*—Firm, similar to cling peach.
- *Ripens.*—Relatively even.
- *Flavor.*—Good sweet taste.
- *Aroma.*—Pleasant.
- *Eating quality.*—Excellent.
- *Color.*—Yellow (14c) to (13c). Pit cavity pink yellow (15c).

Stone:
- *Type.*—Freestone.
- *Size.*—Average length — 1⅜". Average width — 15/16". Average thickness — 1½".
- *Form.*—Ovid.
- *Base.*—Straight.
- *Apex.*—Pointed.
- *Sides.*—Nearly equal.
- *Surface.*—Irregularly furrowed.
- *Color.*—Brown to reddish brown.
- *Tendency to crack.*—None.

Use: Desert.

Shipping quality: Excellent.

Keeping quality: Good.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree substantially as illustrated and described of large size, vigorous and upright in growth and a regular and productive bearer of large size, yellow flesh freestone fruit with good flavor and eating quality; and being further characterized by a partially showy blossom when in full bloom; and a fruit of substantially spheroidal shape having a firm flesh, and a red skin color cover over 80% of the fruit at maturity which occurs about 4 days after maturity of the Redhaven peach.

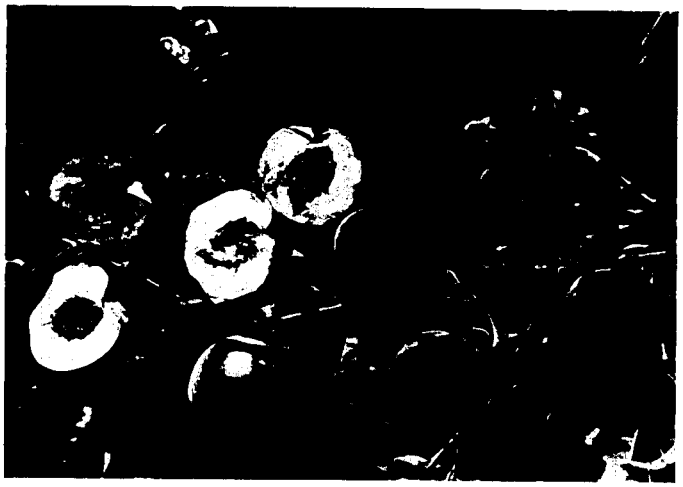

* * * * *